(12) United States Patent
Gurjar et al.

(10) Patent No.: US 9,475,799 B1
(45) Date of Patent: Oct. 25, 2016

(54) SYNTHESIS OF RALTEGRAVIR

(71) Applicant: Emcure Pharmaceuticals Limited, Bhosari, Pune (IN)

(72) Inventors: Mukund Keshav Gurjar, Maharashtra (IN); Swapnil Panditrao Sonawane, Maharashtra (IN); Golakchandra Sudarshan Maikap, Maharashtra (IN); Gulabrao Dagadu Patil, Maharashtra (IN); Shivnath Bhaupatil Shinde, Maharashtra (IN); Pankaj Shalikrao, Maharashtra (IN); Samit Satish Mehta, Maharashtra (IN)

(73) Assignee: Emcure Pharmaceuticals Limited (IN)

( * ) Notice: Subject to any disclaimer, the term of this patent is extended or adjusted under 35 U.S.C. 154(b) by 0 days.

(21) Appl. No.: 15/195,477

(22) Filed: Jun. 28, 2016

Related U.S. Application Data

(62) Division of application No. 14/368,460, filed as application No. PCT/IN2012/000835 on Dec. 21, 2012, now Pat. No. 9,403,809.

(30) Foreign Application Priority Data

Dec. 26, 2011 (IN) .......................... 3664/MUM/2011

(51) Int. Cl.
    *C07D 271/10* (2006.01)
    *C07D 413/12* (2006.01)

(52) U.S. Cl.
    CPC .................. *C07D 413/12* (2013.01)

(58) Field of Classification Search
    CPC ............................ C07D 271/10; C07D 413/12
    See application file for complete search history.

(56) References Cited

U.S. PATENT DOCUMENTS 7,169,780 B2 * 1/2007 Crescenzi .......... C07D 239/557
    514/235.8

FOREIGN PATENT DOCUMENTS

WO    2006060730    6/2006

OTHER PUBLICATIONS

Patil et al., caplus an 2012:1030803, 2012.*
Patil et al.—1,caplus an 2012:1030803, 2012.*
Li et al., 2010, caplus an 2010:806363.*
Humphrey, Guy R. et al., Development of a Second-Generation, Highly Efficient Manufacturing Route for the HIV Integrase Inhibitor Raltegravir Potassium, Organic Process Research & Development, 2011, pp. 73-83, vol. 15, No. 1.
Summa, Vincenzo et al., Discovery of Raltegravir, a Potent Selective Orally Bioavailable HIV-Integrase Inhibitor for the Treatment of HIV-AIDS Infection, Journal of Medicinal Chemistry, 2008, pp. 5843-5855, vol. 15, No. 18.
Li et al., 2010 Caplus an 2010:806363.
Wang et al., European Journal of Medicinal Chemistry, 2012, 50, pp. 361-369.

* cited by examiner

*Primary Examiner* — Sun Jae Yoo
(74) *Attorney, Agent, or Firm* — Florek & Endres PLLC

(57) ABSTRACT

The present invention relates to a novel synthetic route for the preparation of raltegravir and pharmaceutically acceptable salts, starting from 2-amino-2-methylpropanenitrile and oxadiazole carbonyl chloride, through the formation of a pyrimidinone intermediate of formula (V).

5 Claims, No Drawings

SYNTHESIS OF RALTEGRAVIR

This application is a divisional application of U.S. Ser. No. 14/368,460, filed on Jun. 24, 2014, now allowed, which is a U.S. National Stage filing under 35 U.S.C. §371 of International Application No. PCT/IN2012/000835, filed on Dec. 12, 2012, which in turn claims priority to Indian Patent Application No. 3664/MUM/2011, filed on Dec. 26, 2011.

FIELD OF THE INVENTION

The present invention relates to a novel and cost-effective method for the preparation of Raltegravir of formula (I) conforming to regulatory specifications. Specifically, the method circumvents the formation of associated impurities, which are encountered in prior art methods.

BACKGROUND OF THE INVENTION

Raltegravir of formula (I), chemically known as N-[(4-fluorophenyl)methyl]-1,6-dihydro-5-hydroxy-1-methyl-2-[1-methyl-1-[[(5-methyl-1,3,4-oxadiazol-2-yl) carbonylamino]ethyl]-6-oxo-4-pyrimidinecarboxamide is a human immunodeficiency virus (HIV) integrase strand transfer inhibitor which in combination with other antiretroviral agents is indicated for the treatment of HIV-1 infection in adult patients already undergoing treatment and are having evidence of viral replication and HIV-1 strains resistant to multiple antiretroviral agents. The potassium salt of Raltegravir having proprietary name Isentress is administered orally as a tablet of 400 mg strength.

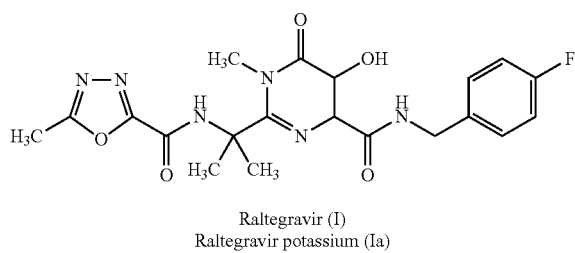 [SMILES: Cc1nnc(C(=O)NC(C)(C)C2=NC(C(=O)NCc3ccc(F)cc3)C(O)C(=O)N2C)o1]

Raltegravir (I)
Raltegravir potassium (Ia)

Various researchers have attempted to synthesize the active pharmaceutical ingredient of formula (I) and its pharmaceutically acceptable salt. Journal of Medicinal Chemistry 2008, 51, 5843-5855 as well as WO 2006060730 discloses a method for the preparation of raltegravir starting from 2-amino-2-methylpropanenitrile. However, the method has a serious drawback, involving formation of up to 22% of O-methyl impurity during the N-methylation of the pyrimidinone ring with Mg(OCH$_3$). The removal of O-methylated impurity requires several purifications involving recrystallization and/or column chromatography, which ultimately reduces the overall yield considerably. Further, the synthetic route also results in the formation of another associated impurity during the preparation of raltegravir free base due to the O-acylation of the penultimate intermediate with oxadiazole carbonylchloride. Thus the formation of several associated impurities and their removal either by chromatographic purification or by successive crystallizations results in loss of yield which ultimately makes the process unviable for commercial use.

Organic Process Research & Development 2011, 15, 73-83 provides another circuitous method for preparation of raltegravir, wherein two methods have been disclosed for the preparation of hydroxy pyrimidinone. The document mentions that the yield of hydroxy pyrimidinone is dependent on the E/Z configuration of the compound obtained by reaction of amidoxime with dimethyl acetylene dicarboxylate. Higher yield (72%) is obtained with the Z isomer while lower yield (48%) is obtained with the corresponding E-isomer. Further, the method involves additional steps of protection and deprotection of the amino and hydroxyl group thereby, making the method lengthy and less attractive for industrial scale.

The reference also reports another method for the methylation of hydroxy pyrimidinone with trimethyl sulfoxonium iodide/magnesium hydroxide without any mention about the reaction solvent and discloses that the reaction provides ≈99% of the desired N-methyl compound after prolonged heating of the reaction mixture at high temperatures, which in turn is likely to give rise to impurities.

Thus the prior art methods are associated with lengthy and circuitous synthetic routes, which not only consume more time for each batch run but also generates associated impurities thereby requiring additional steps of purification. Regulatory authorities all over the world have very stringent norms for permissible limits of such impurities in either the active ingredient or the final formulation.

Therefore, it was imperative for the synthetic chemists to control such impurities below detectable limits during synthesis and develop a route involving a cost-effective process which did not require additional steps of purification. Hence, to overcome the prior art drawbacks, the present inventors developed a new synthetic route for raltegravir, which involves lesser number of synthetic steps, controls the level of undesired impurities below permissible limits and is cost-effective, environmental friendly for convenient implementation on an industrial scale.

OBJECTS OF THE INVENTION

The main object of the invention is to provide an industrially viable method for preparing raltegravir and its pharmaceutically acceptable salts, conforming to regulatory specification.

Another object of the present invention is to provide a novel synthetic route for preparation of raltegravir and its pharmaceutically acceptable salts, which circumvents the formation of impurities and undesired isomers encountered in prior art.

SUMMARY OF THE INVENTION

The main aspect of the present invention is to provide a convenient synthetic route for the preparation of raltegravir and its salts, which confirms to regulatory specification.

Another aspect of the present invention is to provide a method for preparation of raltegravir comprising
  i) reaction of 2-amino-2-methylpropanenitrile with oxadiazole carbonylchloride to give N-(2-cyanopropan-2-yl)-5-methyl-1,3,4-oxadiazole-2-carboxamide (II);
  ii) treating N-(2-cyanopropan-2-yl)-5-methyl-1,3,4-oxadiazole-2-carboxamide (II) with hydroxyl amine (IIIa) or N-methyl hydroxylamine (IIIb) to give N-[(1Z)-1-amino-1-(hydroxyimino)-2-methylpropan-2-yl]-5-methyl-1,3,4-oxadiazole-2-carboxamide (IVa) or N-{1-[hydroxyl(methyl)amino]-1-imino-2-methylpropen-2-yl}-5-methyl-1,3,4-oxadiazole-2-carboxamide (IVb),
  iii) reaction of compound of formula (IVa) or (IVb) with dialkyl acetylene dicarboxylate to give methyl-2-(2-(5- methyl-1,3,4-oxadiazole-2-carboxamido)propan-2-yl)-1,6-dihydro-5-hydroxy-6-oxopyrimidine-4-carboxylate (Va), iv) reaction of compound of formula (Va) with p-fluorobenzylamine to give N-(4-fluorobenzyl)-2-(2-(5-methyl-1,3,4-oxadiazole-2-carboxamido) propan-2-yl)-1,6-dihydro-5-hydroxy-6-oxopyrimidine-4-carboxamide (VI), v) methylating compound of formula (VI) with a methylating agent to give raltegravir (I).

Yet another aspect of the invention is to provide a method which is efficient, cost effective, environmentally friendly and industrially viable.

DETAILED DESCRIPTION OF THE INVENTION

The present inventors have developed a novel synthetic route which overcomes the serious drawbacks of prior art such as:

(i) formation of undesired O-methylated derivatives during methylation of the pyrimidinone nitrogen;

(ii) circumventing the preparation of a mixture of E/Z isomer obtained by reaction of an amidoxime derivative with dialkyl acetylene dicarboxylate;

(iii) reducing the number of steps for preparation of raltegravir thereby making the process cost effective and considerably reducing the time taken for each batch run and (iv) obtaining raltegravir of desired purity without the formation of undesired impurity formed in the prior art.

One embodiment of the present invention relates to a novel synthetic route for preparation of raltegravir and its salts. The synthetic sequence for preparation of raltegravir is represented in Scheme I.

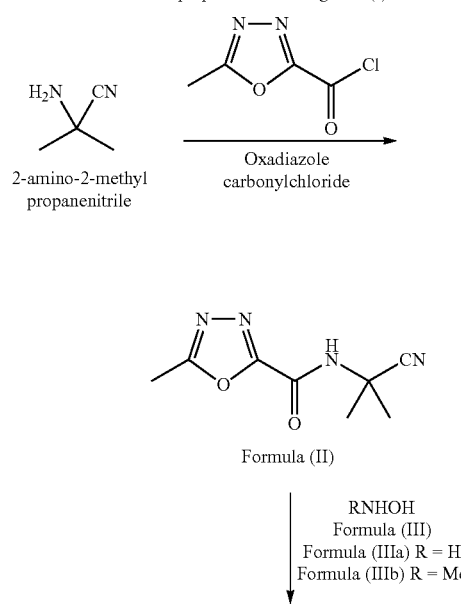

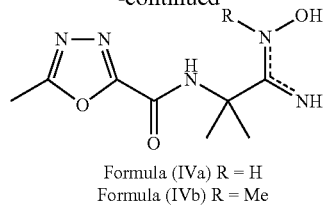

Formula (IVa) R = H
Formula (IVb) R = Me

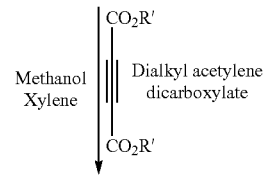

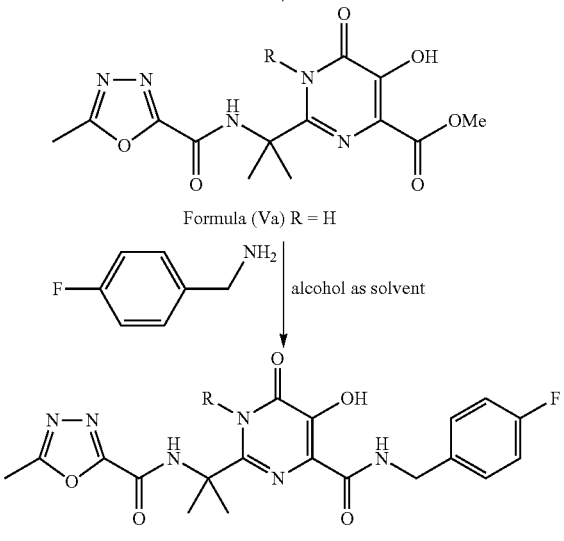

Formula (Va) R = H

Formula (VI) (R-H)

Formula (VI) (R-H) 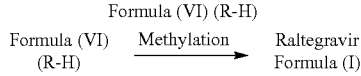 Raltegravir Formula (I)

The present invention relates to a novel synthetic route for preparation of raltegravir comprising reaction of 2-amino-2-methylpropanenitrile with oxadiazole carbonyl chloride in presence of a base. The latter reagent acts as a protecting group for the amino functional group and does not require to be deprotected at any stage of raltegravir synthesis.

The protection of the amino group which is carried out in presence of a base utilizes a halogenated hydrocarbon as solvent such as dichloromethane, dichloroethane, chloroform etc. The solvent is preferably dichloromethane.

The base utilized is selected from an organic base like N-methyl morpholine (NMM), pyridine, N,N-dimethylamino pyridine (DMAP) etc. The amount of base used is in the range of 0.99 to 1.50 moles per mole of 2-amino-2-methylpropanenitrile used in the reaction.

After completion of reaction at a temperature ranging from −5° C. to +10° C., the reaction mixture was concentrated and the N-(2-cyanopropan-2-yl)-5-methyl-1,3,4-oxadiazole-2-carboxamide (II) was separated out from the residue by addition of an alcohol such as methanol, ethanol, isopropanol to the residue. N-(2-cyanopropan-2-yl)-5-methyl-1,3,4-oxadiazole-2-carboxamide (1) is obtained with yield in the range of 90 to 95%.

The amino protected N-(2-cyanopropan-2-yl)-5-methyl-1,3,4-oxadiazole-2-carboxamide (II) is then treated with a hydroxylamine of formula (IIIa) or its methyl derivative of formula (IIIb) to give the respective amidoxime N-[(1Z)-1-amino-1-(hydroxyimino)-2-methylpropan-2-yl]-5-methyl-1,3,4-oxadiazole-2-carboxamide (IVa) or imine derivative N-{1-[hydroxyl(methyl)amino]-1-imino-2-methylpropan-2-yl}-5-methyl-1,3,4-oxadiazole-2-carboxamide (IVb).

The reaction was carried out in alcohol as solvent. The alcohol was selected from the group comprising of methanol, ethanol, isopropanol etc.

Hydroxylamine (IIIa) or N-methyl hydroxylamine (IIIb) was added to the mixture and the resultant mixture heated at 45 to 60° C. till completion of reaction. The reaction mixture was cooled to 0° C. and diluted with a non-polar solvent selected from the group comprising of an aliphatic hydrocarbon, aromatic hydrocarbon, which in turn was selected from the group comprising of hexane, cyclohexane, heptane, toluene, xylene etc.

The product of formula (IVa) or (IVb) separating out quantitatively was filtered and dried.

N-[(1Z)-1-amino-1-(hydroxyimino)-2-methylpropan-2-yl]-5-methyl-1,3,4-oxadiazole-2-carboxamide (IVa) was then treated with dialkyl acetylene dicarboxylate and cyclized to provide pyrimidinone methyl 2-(2-(5-methyl-1,3,4-oxadiazole-2-carboxamido)propan-2-yl)-1,6-dihydro-5-hydroxy-6-oxopyrimidine-4-carboxylate (Va).

The compound of formula (IVa) was added to an alcohol selected from the group comprising of methanol, ethanol, isopropanol etc and refluxed till completion of reaction.

The mixture was cooled between 0 and 30° C. and dimethylacetylene dicarboxylate was added gradually to the mixture.

The amount in moles of dimethylacetylene dicarboxylate added with respect to compound of formula (IVa) was between 0.9 moles and 2.0 moles.

The reaction mixture was stirred for 2-3 hours and concentrated. The residue was diluted with an aromatic hydrocarbon selected from the group comprising of toluene, xylene etc and heated between a temperature of 110° C. and 140° C. till completion of reaction.

The mixture was then cooled between 50 and 70° C. and diluted with a mixture of an alcohol and ether.

The alcohol was selected from the group comprising of methanol, ethanol, isopropyl alcohol etc while the ether was selected from the group comprising of dimethoxyethane, tetrahydrofuran, diisopropyl ether, methyl tert-butyl ether etc.

Compound of formula (Va) thus separating out was filtered and dried.

Methyl-2-(2-(5-methyl-1,3,4-oxadiazole-2-carboxamido) propan-2-yl)-1,6-dihydro-5-hydroxy-6-oxopyrimidine-4-carboxylate (Va) on amidation with p-fluorobenzyl amine in presence of a base gave N-(4-fluorobenzyl)-2-(2-(5-methyl-1,3,4-oxadiazole-2-carboxamido)propan-2-yl)-1,6-dihydro-5-hydroxy-6-oxopyrimidine-4-carboxamide (VI).

The compound of formula (Va) was converted to raltegravir by suspending it in an alcohol selected from the group comprising of methanol, ethanol, isopropyl alcohol etc.

4-Fluorobenzyl amine was added to the mixture and stirred between 75-90° C.

The amount of 4-Fluorobenzyl amine added was between 1.0 mole and 2.5 moles per mole of compound of formula (Va).

After completion of the reaction, the mixture was cooled between 55 and 75° C. and quenched with aqueous acetic acid. The demethylated Raltegravir intermediate of formula (VI) separated out, which was filtered and washed.

N-(4-fluorobenzyl)-2-(2-(5-methyl-1,3,4-oxadiazole-2-carboxamido)propan-2-yl)-1,6-dihydro-S-hydroxy-6-oxopyrimidine-4-carboxamide (VI) was then alkylated with a methylating agent to give raltegravir of formula (I).

The methylating agent was selected from the group comprising of methyl iodide, trimethylsulfoxonium iodide, formic acid/formaldehyde, methyl trifluoromethanesulfonate, dimethyl sulfate, dimethyl zinc, trimethyloxonium tetrafluroborate.

In a specific embodiment, the raltegravir intermediate of formula (VI) was treated with a methylating agent such as trimethysulfoxonium iodide at 100° C. till completion of reaction and cooled between 5 and 25° C. The reaction mixture was quenched with aqueous sodium bisulfite and extracted with a chlorinated solvent such as dichloromethane. The organic layer was separated, concentrated and the residue was crystallized from aqueous methanol to provide raltegravir (1) having the desired purity.

Among the advantages of the novel route of synthesis of raltegravir is the regioselective methylation of N-(4-fluorobenzyl)-2-(2-(5-methyl-1,3,4-oxadiazole-2-carboxamido) propan-2-yl)-1,6-dihydro-5-hydroxy-6-oxopyrimidine-4-carboxamide (VI) obtained by amidation of methyl-2-(2-(5-methyl-1,3,4-oxadiazole-2-carboxamido)propan-2-yl)-1,6-dihydro-5-hydroxy-6-oxopyrimidine-4-carboxylate (Va) with p-fluorobenzyl amine. The methylation reaction provides regioselectivity of more than 99% as against methylation of oxygen at 6' position, thereby resulting in a higher yield of more than 90%. The yield for the methylation reaction is in the range of 88 to 90%.

On the other hand, prior art methods provide a 7:3 ratio of the 1-nitrogen methylated 6-oxygen methylated product after methylation.

Further, the protection of 5-hydroxy group with pivaloyl chloride or benzoic anhydride before methylation reaction is avoided. The prior art method requires additional step for deprotection which increase the cost and time for each batch run.

Thus, the invention is free from the additional steps of protection and deprotection of amino protecting group and also provides a simple, economically and efficient method for preparing raltegravir with desired purity.

The preparation of pyrimidinone methyl 2-(2-(5-methyl-1,3,4-oxadiazole-2-carboxamido)propan-2-yl)-1,6-dihydro-5-hydroxy-6-oxopyrimidine-4-carboxylate (Va), by treating with dialkyl acetylene dicarboxylate and cyclizing has an advantage over prior art, as the yields were increased by 10 to 15%.

Thus, the present invention based on the above advantages satisfies the need for developing an alternate synthetic route for raltegravir which has minimum number of steps and cost effective and environmental friendly and easily implemented industrially.

Raltegravir (I) thus obtained has purity above 99.5% with an over all yield ranging from 55 to 58% based on the starting material.

The present invention is a novel synthetic route for the preparation of raltegravir which has the following advantages over prior art methods:

The present synthetic route avoids the use of protection and deprotection steps of amine group as used in the prior art methods;

Increase in the yield of pyrimidinone, methyl 2-(2-(5-methyl-1,3,4-oxadiazolo-2-carboxamido)propan-2-yl)-1,6-dihydro-5-hydroxy-6-oxo pyrimidines-4-carboxylate (Va), an important intermediate for the synthesis of raltegravir Methylation of N-(4-fluorobenzyl)-2-(2-(5-methyl-1,3,4-oxadiazole-2-carboxamido)propan-2-yl)-1,6-dihydro- 5-hydroxy-6-oxopyrimidine-4-carboxamide (VI) at nitrogen reveals regioselectivity of more than 99% over oxygen methylation, Synthetic route is cost-effective, environmentally friendly and easily implemented on an industrial scale.

The principles, preferred embodiments and modes of operation of the present invention have been described in the foregoing specification. The invention which is intended to be protected herein, however should not to be construed to be limited to the particular forms disclosed, since these are to be regarded as illustrative rather than restrictive. Variations and changes may be made by those skilled in the art, without departing from the spirit of the invention.

The present invention is described herein below with reference to examples, which are illustrative only and should not be construed to limit the scope of the present invention in any manner.

EXAMPLES

Example 1

Preparation of N-(2-cyanopropan-2-yl)-5-methyl-1,3,4-oxadiazole-2-carboxamide (II)

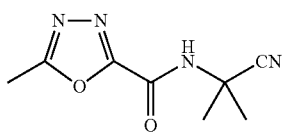

Formula (II)

2-Amino-2-methylpropanenitrile (90 gms) was suspended in dichloromethane (90 ml) and N-methyl morpholine (1.10 moles) was added with stirring. A mixture of oxadiazole carbonyl chloride (90 gms) in dichloromethane (100 ml) was added drop wise to the suspension at 0 to 5° C. The reaction mixture was stirred and monitored by thin layer chromatography (TLC). The reaction mass was concentrated under reduced pressure after completion of reaction. The product separated out on addition of isopropyl alcohol (500 ml), which was then filtered and dried.

Yield: 72 gins (70%).

$^1$H NMR (400 MHz, CDCl$_3$): δ 7.34 (br s, 1H), 2.64 (s, 3H), 1.84 (s, 6H);

$^{13}$C NMR (100 MHz, CDCl$_3$): δ 166.69, 158.41, 152.80, 119.90, 47.42, 27.13, 11.40;

MS (CI): Calculated [for C$_8$H$_{10}$N$_4$O$_2$ (M$^+$H)/z: 195.19]. found: (M$^+$H)/z: 195.1.

Melting point: 142-145° C.

Example 2

Preparation of N-[(1Z)-1-amino-1-(hydroxyimino)-2-methylpropan-2-yl]-5-methyl-1,3,4-oxadiazole-2-carboxamide (IVa)

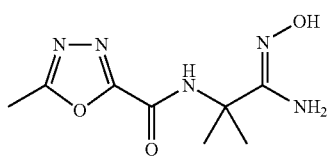

Formula (IVa)

N-(2-cyanopropan-2-yl)-5-methyl-1,3,4-oxadiazole-2-carboxamide (II) (185 gms) was suspended in isopropyl alcohol (462 ml), heated to 50 to 55° C. Aqueous hydroxylamine (IIIa; 76 ml) was added and the reaction mixture stirred for 30 minutes at 60° C. After completion, reaction mass was cooled between 0 and 5° C. and heptane (462 ml) was added to the reaction mass. The resultant slurry was filtered, washed with heptane (185 ml) and the wet cake was dried to give N-[(1Z)-1-amino-1-(hydroxyimino)-2-methylpropan-2-yl]-5-methyl-1,3,4-oxadiazole-2-carboxamide (IVa).

Yield: 198 gms (94%).

$^1$H NMR (400 MHz, DMSO d$^6$): δ 9.36 (br s, 1H), 8.75 (s, 1H), 7.43 (br s, 1H), 5.58 (s, 2H), 2.55 (s, 31), 1.55 (s, 6H);

$^{13}$C NMR (100 MHz, DMSO d$^6$) δ 165.63, 138.91, 155.13, 151.76, 54.95, 24.86, 10.74;

MS (CI): Calculated [for C$_8$H$_{13}$N$_5$O$_3$ (M z: 228.22]. found: (M$^+$H)/z: 228.1.

Melting point: 140-150° C.;

Example 3

Preparation of methyl-2-(2-(5-methyl-1,3,4-oxadiazole-2-carboxamido)propan-2-yl)-1,6-dihydro-5-hydroxy-6-oxopyrimidine-4-carboxylate (Va)

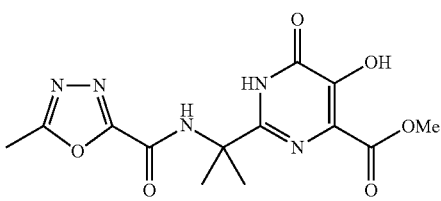

Formula (Va)

N-[(1Z)-1-amino-1-(hydroxyimino)-2-methylpropan-2-yl]-5-methyl-1,3,4-oxadiazole-2-carboxamide (IVa) (198 gins) was suspended in methanol (1188 ml) and cooled to 15 to 25° C. Dimethyl acetylenedicarboxylate (DMAD; 152.8 gins) was added and the reaction mass was stirred for 2 to 3 hours at 25° C. The reaction mass was concentrated under reduced pressure and xylene was added and stirred between 135° C. and 125° C. for 6 hour. After completion of reaction, the mixture was cooled to 60° C. and methanol (170 ml) & methyl tert-butyl ether (MTBE) were added to the reaction mass and stirred for 1 hour. The resultant slurry was filtered and washed with a 9:1 mixture of methanol & methyl tert-butyl ether (MTBE) and dried to give methyl 2-(2-(5-methyl-1,3,4-oxadiazole-2-carboxamido)propan-2-yl)-1,6-dihydro-5-hydroxy-6-oxopyrimidine-4-carboxylate (Va).

Yield: 198 gins (66%).

$^1$H NMR (400 MHz, DMSO d$^6$): δ 12.74 (s, 1H), 10.35 (s, 1H), 9.12 (s, 1H), 3.81 (s, 3H), 2.58 (s, 3H), 1.59 (s, 6H);

$^{13}$C NMR (100 MHz, DMSO d$^6$): δ 166.60, 166.15, 160.19, 159.23, 153.26, 152.87, 145.65, 128.30, 56.60, 52.91, 26.26, 11.34;

MS (CI): Calculated [for C$_{13}$H$_{15}$N$_5$O$_6$ (M+H)/z: 338.29]. Found: (M$^+$H)/z: 338.2.

Melting Point 229-234° C.;

Example 4

Preparation of N-(4-fluorobenzyl)-2-(2-(5-methyl-1,3,4-oxadiazole-2-carboxamido)propan-2-yl)-1,6-dihydro-5-hydroxy-6-oxopyrimidine-4-carboxamide (VI)

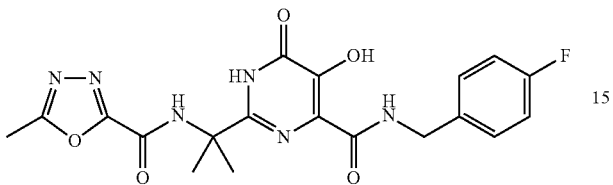

Formula (VI)

Methyl 2-(2-(5-methyl-1,3,4-oxadiazole-2-carboxamido) propan-2-yl)-1,6-dihydro-5-hydroxy-6-oxopyrimidine-4-carboxylate [V(a); 40 gms] was suspended in isopropyl alcohol (400 ml) and 4-fluorobenzyl amine (30 gins) was added to the above mixture. The reaction mixture was stirred at 80 to 85° C. After completion, reaction mass was cooled to 60° C. and acetic acid (1600 ml) and water (400 ml) was added. The resultant crystalline product was filtered and washed with mixture of water and isopropyl alcohol (1:1) and dried to give N-(4-fluorobenzyl)-2-(2-(5-methyl-1,3,4-oxadiazole-2-carboxamido) propan-2-yl)-1,6-dihydro-5-hydroxy-6-oxopyrimidine-4-carboxamide VI).

Yield: 46 gms (90%).

$^1$H NMR (400 MHz, DMSO d$^6$) δ 12.54 (s, 1H), 12.34 (s, 1H), 9.20-9.18 (t, 1H), 9.04 (s, 1H), 7.40-7.37 (m, 21), 7.19-7.14 (m, 2H), 4.50-4.48 (d, 2H), 2.58 (s, 3H), 1.63 (s, 61);

$^{13}$C NMR (100 MHz, DMSO d$^6$) δ 149.95, 145.26, 132.66, 131.75, 128.54, 128.36, 126.11, 125.10, 119.70, 117.16, 115.94, 109.62, 47.87, 47.68, 45.30, 42.90;

MS (CI): Calculated [for $C_{19}H_{19}FN_6O_5$ (M$^+$H)/z: 431.39]. found: (M$^+$H)/z: 431.2.

Melting point: 213-216° C.;

Example 5

Preparation of Raltegravir (I)

N-(4-fluorobenzyl)-2-(2-(5-methyl-1,3,4-oxadiazole-2-carboxamido) propan-2-yl)-1,6-dihydro-5-hydroxy-6-oxopyrimidine-4-carboxamide (VI) (50 gins), magnesium hydroxide (13.9 gms) trimethylsulfoxonium iodide (52.4 gms) and water (1.3 ml) were heated to 100° C. for 7 hour. The reaction was cooled to 20° C. and stirred for 15 minutes. An aqueous solution of sodium bisulfate (2M; 5 ml) was added and stirred for 30 to 45 minutes at 25 to 35° C., reaction mass was extracted with dichloromethane (400 ml) and solvent concentrated under reduced pressure. The product was isolated by crystallization from mixture of methanol-water (1:1. The resultant slurry was filtered and washed with mixture of methanol-water (50 ml) and dried to give Raltegravir (I).

Yield: 46 gms

Yield: 94%.

We claim:

1. A compound of formula:

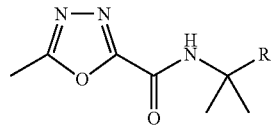

wherein R is CN;

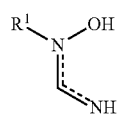

wherein R' is H or CH$_3$;

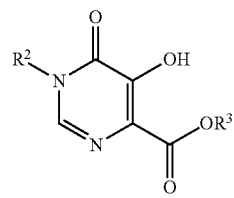

wherein R$^2$ is H and R$^3$ is C$_{1-4}$ alkyl group; or

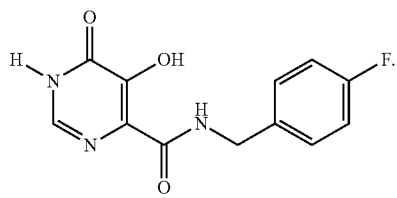 [SMILES: O=C(NCc1ccc(F)cc1)c1nc[nH]c(=O)c1O]

2. A compound as recited in claim 1 of the formula

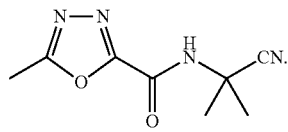

3. A compound as recited in claim 1 of the formula

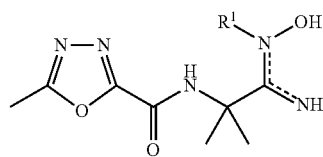

wherein R' is H or CH$_3$.

4. A compound as recited in claim 1 of the formula
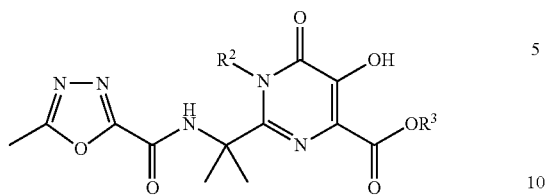
wherein R² is H and R³ is $C_{1-4}$ alkyl group.
5. A compound as recited in claim 1 of the formula
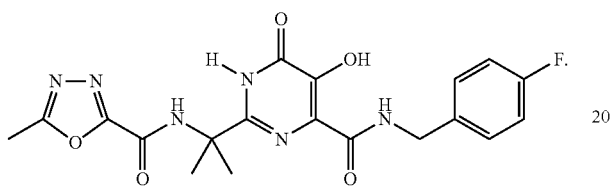
* * * * *